United States Patent
Handal-Vega et al.

(10) Patent No.: US 6,278,014 B1
(45) Date of Patent: Aug. 21, 2001

(54) SYNTHETIC PROCEDURE FOR THE MANUFACTURE OF ASPIRIN

(75) Inventors: Erlinda Handal-Vega, San Salvador (SV); Andre Patrick Denis Loupy, Gambauderie (FR); Jorge Manuel Collazo Garcia, San Salvador (SV)

(73) Assignee: Manufacturas Humberto Buelee Hijos, S.A. de C.V., San Salvador (SV)

( * ) Notice: Subject to any disclaimer, the term of this patent is extended or adjusted under 35 U.S.C. 154(b) by 0 days.

(21) Appl. No.: 09/587,803

(22) Filed: Jun. 6, 2000

Related U.S. Application Data

(63) Continuation-in-part of application No. PCT/IB98/02083, filed on Dec. 18, 1998.

(30) Foreign Application Priority Data

Dec. 18, 1997 (SV) ......................................... 011997000108

(51) Int. Cl.$^7$ .................................................... C07C 69/00
(52) U.S. Cl. .............................................................. 560/143
(58) Field of Search ............................................. 560/143

(56) References Cited

U.S. PATENT DOCUMENTS 3,373,187   3/1968   Edmunds et al. .

*Primary Examiner*—Paul J. Killos
*Assistant Examiner*—John N. Calve
(74) *Attorney, Agent, or Firm*—Sughrue, Mion, Zinn, Macpeak & Seas, PLLC

(57) ABSTRACT

The present invention provides a method for the synthesis of acetyl salicylic acid comprising mixing acetic anhydride and salicylic acid in approximately or exactly stoichiometric proportions and calcium oxide or zinc oxide, obtaining a yield of a mixture of acetyl salicylic acid and calcium acetate or zinc acetate with 2% maximum of free salicylic acid content. The reaction is fast, exothermic, one-pot, non-pollutant of the environment due to the fact that it doesn't require elimination of acid residues nor requires the use of any type of organic solvent (other than such solvent activity provided by the reactants themselves), and doesn't require recrystallization since it yields a dense product which can be mixed with the common excipients for acetyl salicylic acid and compressed into tablets immediately after the synthesis process.

13 Claims, 3 Drawing Sheets

IR SPECTRUM OF PRODUCT REACTION BETWEEN SALICYLIC ACID AND ACETIC ANHYDRIDE IN PRESENCE ON ZINC OXIDE.

SYNTHETIC PROCEDURE FOR THE MANUFACTURE OF ASPIRIN

This application is a continuation-in-part application of PCT/IB98/02083 filed Dec. 18, 1998, claiming priority from S.V. 011997000108 filed Dec. 18, 1997.

BACKGROUND OF THE INVENTION

1. Field of the Invention

The current invention relates to the field of pharmaceutical synthesis and the preparation of acetyl salicylic acid. A synthetic procedure is shown which is elegant in its simplicity and its ability to provide a product, which does not require any purification of the final reaction product before being used in pharmaceutical preparations. The reaction is very fast, one-pot, non-polluting of the environment, and provides 100% yield of product which contains 2% maximum of free salicylic acid.

2. Background of the Art

Acetyl salicylic acid, commonly known as aspirin, has been the most successful pharmaceutical product in the world. Its original benefits as an analgesic and fever reducing agent continue to be recognized today, and new and even more significant benefits have been found in recent years. Acetyl salicylic acid has been found to reduce the likelihood of strokes, reduce the likelihood of heart attacks, reduce the complications of a stroke or heart attack when administered after the cardiovascular incident, and reduce the likelihood of second heart attack. With only minimal side effects or complications, it is the most widely used pharmaceutical agent in the world, and its range of use continues to grow.

The original U.S. patent covering the compound acetyl salicylic acid is U.S. Pat. No. 644,077, issued Feb. 27,1900, in the name of Felix Hoffman. The Hoffman Patent describes that the compound exhibits therapeutic properties. A single synthetic procedure for its manufacture is taught, comprising refluxing salicylic acid and acetic anhydride for about two hours at 150 degrees Celsius.

U.S. Pat. No. 671,769 describes a process of producing acetylsalicylic acid by substituting the acetyl group for the hydrogen of the hydroxyl group of salicylic acid and of its derivatives. The reaction is effected by the reciprocal action of salicylic acid and acetic anhydride in the presence of a condensing agent. The condensing agent shown is concentrated sulfuric acid.

U.S. Pat. No. 3,235,583 describes an improved method of synthesizing acetyl salicylic acid without resorting to the use of strong agents. The process is asserted to provide products with high purity and near theoretical yields, without resorting to extreme or repeated recrystallization steps. The process comprises a mixture of salicylic acid and acetic anhydride at 40 to 95° C. employing a molar excess of about 20% of acetic anhydride, reacting the mixture in a closed vacuum equipped vessel at the elevated temperature, maintaining the elevated temperature and reducing the internal pressure to a partial vacuum within the range of about $1.5 \times 10^{-1}$ to $2.2 \times 10^{-1}$ torr and thereafter gradually reducing the pressure to range between about $3.9 \times 10^{-2}$ torr and the minimum attainable pressure, maintaining the elevated temperature and reduced pressure at the lower range for about 1 to 3 hours, and thereafter recovering crystalline acetyl salicylic acid from the reaction vessel. As can be seen from the description provided in the '583 patent, special reaction vessels are needed, pressure within the vessel must be actively controlled, and the process takes a number of hours to complete.

U.S. Pat. No. 3,373,187 describes a method of synthesizing aspirin by the reaction of acetic anhydride and salicylic acid using a catalytic metal salt such as $Mg(OH)_2$. Reaction times of about 2 to 11 hours are shown. Typical catalytic salts in addition to the preferred $Mg(OH)_2$, are said to be nickel hydroxide, calcium nitrate, cobalt nitrate and magnesium acetate. A concentration range for the catalyst is described as 25 to 500 p.p.m. The following chart depicts a partial comparison between the process of U.S. 3,373,187 and the inventive process disclosed herein. In addition, the CaO and/or ZnO used in the present invention forms significant quantity of Ca acetate and/or Zn acetate as a wanted part of the reaction product.

| U.S. PAT. NO. U.S. 3,373,187 REACTION SYSTEM | INVENTIVE REACTION SYSTEM |
| --- | --- |
| 1. Non-stoichiometric synthesis | Stoichiometric synthesis |
| 2. Solvent is needed, such as acetic acid or toluene, benzene and xylene | No solvent is needed |
| 3. Reaction time of at least 2 hours | Short, i.e., 20 minute, reaction time |
| 4. Necessary to heat the reaction system | External heat not required |
| 5. Separation step required after product synthesis for obtaining desired product | Not necessary to carry out a separation step after final product synthesis |
| 6. Distillation, evaporation, needed for obtaining crystals of reaction product | Final reaction product does not need to be distilled |

In the process of the '187 patent, larger amounts of the preferred $Mg(OH)_2$ catalyst would produce significant quantities of water and Mg acetate, which due to its deliquescent character, would cause decomposition of the wanted aspirin reaction product.

SUMMARY OF THE INVENTION

The present invention provides a method for the synthesis of acetyl salicylic acid comprising reacting acetic anhydride and salicylic acid in stoichiometric proportions, along with calcium oxide or zinc oxide, for obtaining a yield of acetyl salicylic acid, and admixed calcium acetate or zinc acetate, with 2% maximum of free salicylic acid content, even after storage. The synthetic procedure comprises a method for obtaining acetyl salicylic acid comprising reacting acetic anhydride, salicylic acid and calcium oxide or zinc oxide. The reaction is heterogeneous, fast, exothermic, one-pot, non-pollutant of the environment due to the fact that it doesn't require elimination of acid residues nor requires the use of any type of organic solvents (other than such solvent activity provided by the reactants themselves), and doesn't require recrystallization since it yields as product a dense mixture of acetyl salicylic acid and calcium acetate or zinc acetate which can be mixed with the conventional excipients for acetyl salicylic acid and compressed into tablets immediately after the synthesis process.

DETAILED DESCRIPTION OF THE INVENTION

Figure 1A:
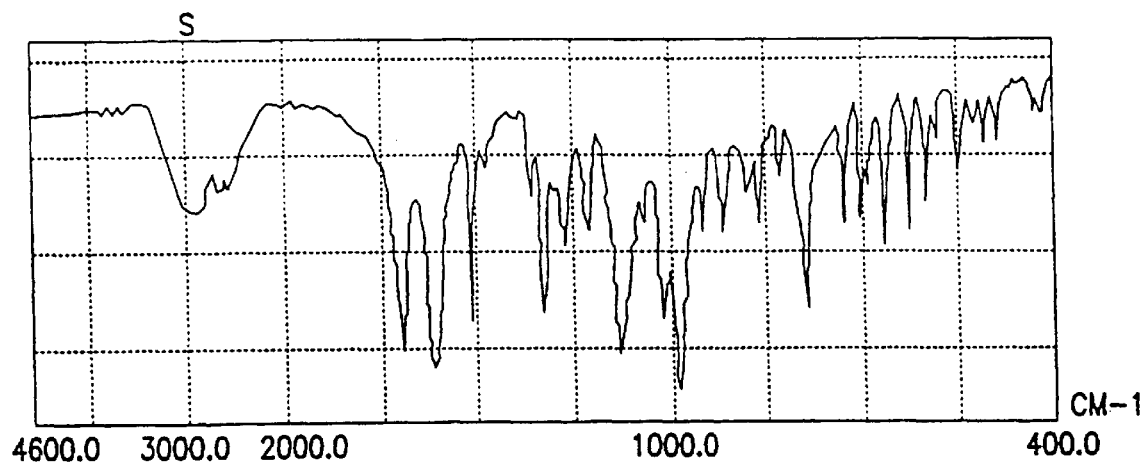
FIGS. 1a and 1b show the Infrared Spectrum of a) acetyl salicylic acid and b) the product "as is" of a synthetic procedure according to the present invention.

The invention describes a novel method for the synthesis of acetylsalicylic acid. Since 1900, when Hoffman received the patent for the manufacture of acetyl salicylic acid from acetic anhydride and salicylic acid, there have been many modifications of the synthesis: Ledeler (1901) added sulfuric acid to the system in order to accelerate the process of esterification. A. Bercy, (Nature, No. 2977, p.462, 1936) further proposed to make this synthesis in the presence of acetic acid as a solvent, heating the system to 90° C. for some time and then cooling to 20° C. Other authors (e.g., E.J.Perry, Chem. Abst. Vol. 10 No. 2121), proposed that during the synthesis process at those temperatures, the ester o-$AcC_6H_4CO_2C_6H_4CO_2H$ is formed and then it is decomposed into acetyl salicylic acid and salicylic acid.

In summary, the methods proposed so far for the synthesis of acetyl salicylic acid include: use of an excess of acetic anhydride or addition of acetic acid to the system as solvent, the addition of a strong acid (e.g., concentrated sulfuric or concentrated phosphoric acid as a catalyst), a subsequent stage of disposal of the sulfuric acid (or phosphoric acid), frequently recrystallization of the obtained product and using metal salt catalysts. Currently, the most used method of obtention at industrial level consists of mixing salicylic acid and acetic anhydride in excess in a pressure reactor at a temperature of 98° C. for 2–3 hours, then the resultant solution is pumped to a filter and cooled to 0° C. to aid the crystallization of the product (e.g., possibly within the practice of U.S. Pat. No. 3,235,583). The suspension is centrifuged and the product crystallized and washed (cf. Kirk Othmer Encyclopedia of Chemical Technology, 1997, on line text, and acetylsalicylic acid [530-75-6]. The reported yield for the proposed methods is about 90%.

The present invention provides a method for the synthesis of acetyl salicylic acid comprising reacting acetic anhydride and salicylic acid in about stoichiometric proportions along with calcium oxide or zinc oxide as a support and acid neutralization agent. When CaO is used a yield of acetyl salicylic acid of no less than 98–99% (2% maximum of free salicylic acid content) and calcium acetate is obtained. The reaction is fast, exothermic, one-pot, non pollutant of the environment due to the fact that it doesn't require elimination of acid residues nor requires the use of any type of organic solvent (other than such solvent activity provided by the reactants themselves), and doesn't require recrystallization since it yields a dense product which can be mixed with the excipients for acetyl salicylic acid and compressed into tablets immediately after the synthesis process. Calcium in the form of calcium acetate is one of the most bioassimilated forms of this element by the human body and is a resultant product from this synthetic route.

CaO and/or ZnO is used in a molar proportion of 0.5 to 0.8 moles per one mole of acetic anhydride. Preferably, acetic anhydride and salicylic acid are used in exact stoichiometric proportion to the degree obtainable on an industrial scale in practice. The reaction product contains about 70% aspirin and about 30% Ca and/or Zn acetate by weight.

One perspective of the value of the process and products of the present invention from the technical and economic point of view and the advantages of the synthesis method for acetyl salicylic acid as compared to previously reported synthetic procedures is understood from one or more of the following aspects:

A. there is no need to add sulfuric acid or phosphoric acid to the reaction system as an acid catalyst of the synthesis,
B. the reaction system doesn't need external heating,
C. solvents are not required in the synthesis process,
D. it is not necessary to add excess reactants to accelerate and/or increase the synthesis yield,
E. the synthesis is very fast, with a high yield,
F. the product obtained is a mixture of acetyl salicylic acid and calcium acetate or zinc acetate, with a maximum free salicylic acid content of about 2%, in a single synthesis step,
G. the synthetic procedure may be performed in a single pot,
H. with each of these features helping to contribute to a low cost process for the production of acetyl salicylic acid,
I. the aqueous solution of the synthesis product, without recrystallization, gives a pH less acid (pH 4.2) than that presented by the aqueous solution of standard acetyl salicylic acid alone (pH 2.6) and commercial acetyl salicylic acid tablet (pH 2.9),
J. a tablet containing acetyl salicylic acid with calcium or zinc can be manufactured directly from the synthetic product without purification,
K. recrystallization of the synthesis product would not be needed for the subsequent manufacture of the tablets, and
L. the synthesis is non-polluting of the environment by not producing waste material and by not using organic solvents.

It is possible to add various materials into the reaction mixture, but the addition of materials which might have to be removed by purification should be avoided so that additional purification steps are not added back into the process. Thus, any additive should be incorporated after the reaction product is obtained.

The final reaction product without any purification process or distilling operation comprises acetyl salicylic acid and calcium acetate or zinc acetate with less than 2% free salicylic acid, preferably less than 1%, by weight of the mixture.

The direct reaction product compositions (the reaction product composition immediately after conclusion of the synthetic reaction and before any purification step has been performed) may also be characterized by the low contents of free salicylic acid.

The CaO and/or ZnO is heat activated by calcination as illustrated in the following examples, for removing water and possible impurities which might otherwise produce excessive free salicylic acid.

EXAMPLES

EXAMPLE 1

In a 100 ml beaker, 1.3680 g acetic anhydride ($13.4 \times 10^{-3}$ mol) and 1.8492 g salicylic acid ($13.4 \times 10^{-3}$ mol) was thoroughly mixed by agitation with glass rod with 0.5628 g calcium oxide ($10.05 \times 10^{-3}$ mol previously calcinated at a temperature from 430 to 850° C. for one hour and subsequently cooled at room temperature in a silicagel desiccant). The calcium oxide was added to the acetic anhydride salicylic acid mixture with vigorous agitation. A dense paste was formed at the beginning, which turned liquid for a couple of minutes and then started to harden and fractionalize into small crystals (agitation was not suspended at any time). The reaction was exothermic, reaching 60–70° C. At the end of the reaction, the system went back to room temperature, and considerably increased in volume (resulting in a volume of approximately three times with reference to the initial volume of the mixture). Duration of the synthesis was 20 min. The synthesis product was identified by the record of UV and IR spectra, which were compared to similar spectrum corresponding to acetyl salicylic acid, calcium oxide and calcium acetate standard samples. The content of free salicylic acid was measured by colorimetry through the formation of a colored complex with Fe. The proportion of free salicylic acid in the product 36 days after synthesis was about 0.9% by weight of the composition.

Figure 1B:
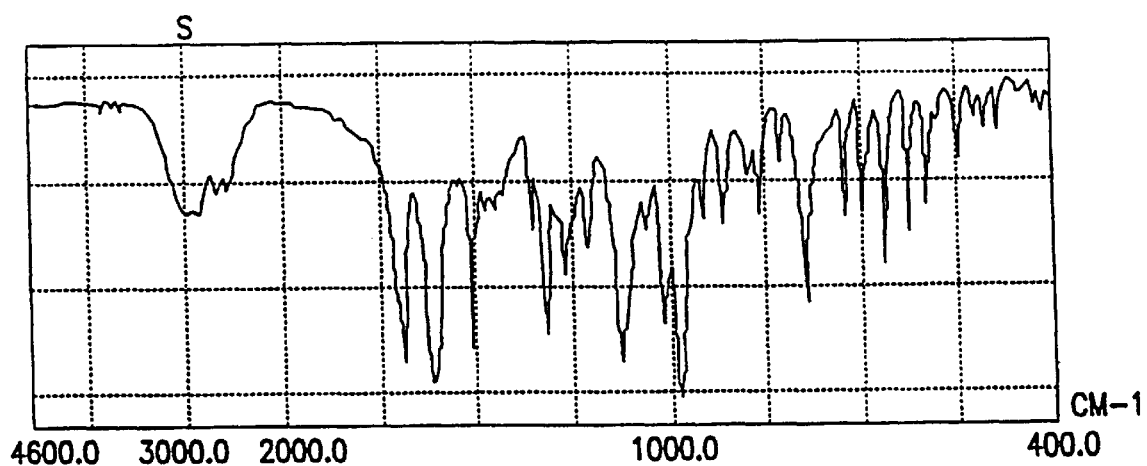

FIG. 1 shows the IR Spectrum of a)acetyl salicylic acid standard; and b) product of this type of synthesis "as it is", without any further crystallization. The reaction product contained about 70% aspirin and 30% Ca acetate, by weight.

EXAMPLE 2

19.0648 g salicylic acid ($1.38 \times 10^{-1}$ mol) was weighed and was mixed with 14.1 mL acetic anhydride ($1.38 \times 10^{-1}$ mol) in a 250 mL beaker. To the mixture, 3.7028 g calcium oxide ($6.6 \times 10^{-2}$ mol, previously treated as in example 1) was added. The two components were thoroughly mixed. The reaction was exothermic. After 25 minutes, the system returned to room temperature, had increased approximately three times its original volume and appeared as a fine white, loose and dense powder. The presence of acetyl salicylic acid was analyzed in the final product, by dissolving a sample in chloroform and recording the UV spectrum. The spectrum was compared to that of salicylic acid and acetyl salicylic acid standard samples and mixture of both in a chloroform vehicle. IR spectra of the synthesis product were recorded and compared to similar spectra of standard samples. The content of salicylic acid was measured by colorimetry by the formation of colored complex with Fe.

The content of free salicylic acid in the product immediately after synthesis was 0% and 138 days after synthesis was 1.9% by total weight of the composition.

Figure 2A:
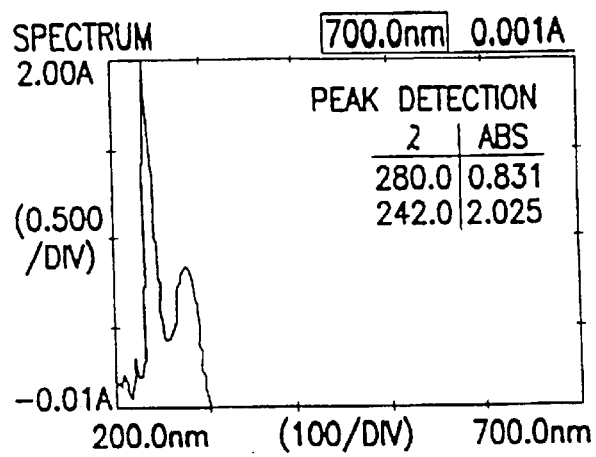
FIGS. 2a and 2c show an UV spectrum of a) acetyl salicylic acid, b) salicylic acid, and c) a freshly synthesized product according to the present invention made with calcium oxide.
Figure 2B:
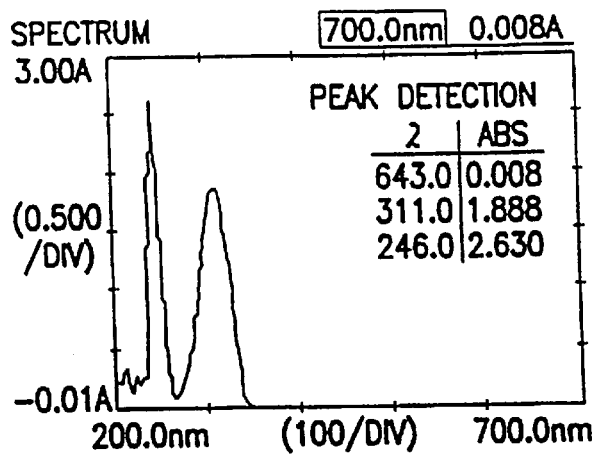
Figure 2C:
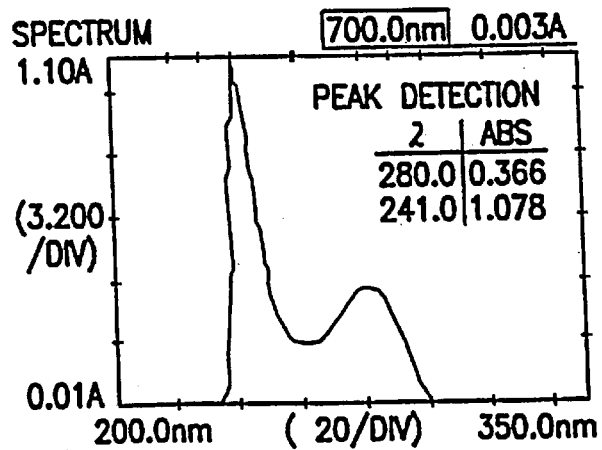

FIG. 2. shows the UV/Visible spectra of a) acetyl salicylic acid standard; b) salicylic acid standard; and c)a freshly synthesized product of the invention.

EXAMPLE 3

In a 100 mL beaker, 1.3974 g acetic anhydride ($1.37 \times 10^{-2}$ mol) and 1.9060 g salicylic acid ($1.37 \times 10^{-2}$ mol) was thoroughly mixed by agitation with a glass rod. 0.8718 g of zinc oxide ($1.07 \times 10^{-2}$ mol, previously calcinated at a temperature from 250 to 700° C. for one hour and subsequently cooled at room temperature in a silicagel desiccant), was added to the first composition with vigorous agitation. A dense liquid was formed for ten minutes and then started to harden. Agitation was not suspended at any time. The reaction was exothermic, and at the end of the exothermic period, the system was allowed to cool to room temperature and considerably increased in volume. Duration of the synthesis was 30 min. The synthesis product was identified by the record of UV and IR spectra, which were compared to similar spectra corresponding to acetyl salicylic acid, zinc oxide and zinc acetate standard samples. The content of free salicylic acid was measured by colorimetry through the formation of colored complex with Fe (III). Content of free salicylic acid in the product was about 1%.

Figure 3:
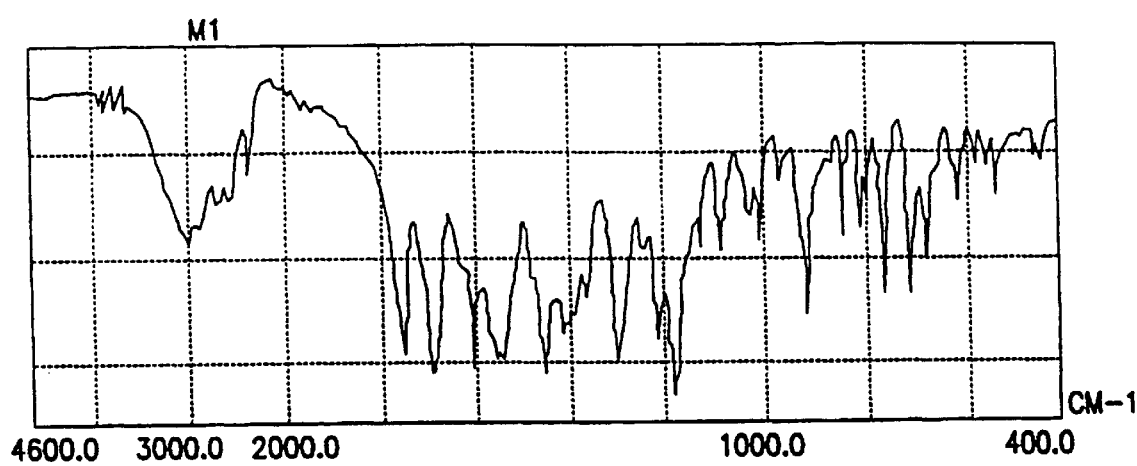
FIG. 3 shows an Infrared Spectrum of a freshly synthesized product according to the present invention made with zinc oxide.

FIG. 3 shows the spectra for the composition resulting from this synthesis.

Variations of the invention will be apparent to the skilled artisan.

What is claimed is:

1. A synthesis method to obtain a reaction product containing acetyl salicylic acid and calcium and/or zinc acetate comprising heterogeneously reacting acetic anhydride, salicylic acid and at least one of calcium oxide and zinc oxide.

2. The synthesis method of claim 1 wherein said acetic anhydride and salicylic acid are heated by an exothermic reaction between acetic anhydride, salicylic acid and at least one of calcium oxide and zinc oxide.

3. The method of claim 2 wherein the method is carried out in the absence of external heat.

4. The method of claim 2 wherein said acetic anhydride and said salicylic acid are present in about stoichiometric proportions.

5. The method of claim 2 wherein the method is carried out in the absence of any added organic solvents.

6. The method of claim 1 wherein said CaO is heat activated CaO.

7. The method of claim 3 wherein said ZnO is heat activated ZnO.

8. The method of claim 3 wherein said acetic anhydride and salicylic acid are thoroughly mixed before addition of the at least one of calcium oxide and zinc oxide.

9. The method of claim 3, wherein at least one of the CaO and ZnO is present as 0.5 to 0.8 molar proportion in relationship to the acetic anhydride.

10. The method of claim 4 wherein the reaction product contains less than 2% free salicylic acid without further purification.

11. The synthesis method of claim 1, wherein calcium oxide is used as a support and acid neutralization agent in two concomitant reactions by which acetyl salicylic acid and calcium acetate are produced.

12. The synthesis method of claim 1, wherein zinc oxide is used as a support and acid neutralization agent in two concomitant reactions by which acetyl salicylic acid and zinc acetate are produced.

13. The synthesis method of claim 4, wherein an exact stoichrometric proportion is used.

* * * * *

UNITED STATES PATENT AND TRADEMARK OFFICE
CERTIFICATE OF CORRECTION

| | | |
|---|---|---|
| PATENT NO. | : 6,278,014 B1 | Page 1 of 1 |
| DATED | : August 21, 2001 | |
| INVENTOR(S) | : Erlinda Handal-Vega, Andre Patrick Denis Loupy and Jorge Manuel Collazo Garcia | |

It is certified that error appears in the above-identified patent and that said Letters Patent is hereby corrected as shown below:

<u>Title page,</u>
Item [73], Assignee, delete "Buelee Hijos" and insert -- Bukelee Hijos --.

Signed and Sealed this

Tenth Day of September, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,278,014 B1                                                        Page 1 of 1
DATED         : August 21, 2001
INVENTOR(S)   : Erlinda Handal-Vega, Andre Patrick Denis Loupy and Jorge Manuel Collazo Garcia It is certified that error appears in the above-identified patent and that said Letters Patent is hereby corrected as shown below:

<u>Title page,</u>
Item [73], Assignee, delete "Buelee Hijos" and insert -- Bukele e Hijos --.

This certificate supersedes Certificate of Correction issued September 10, 2002

Signed and Sealed this

Twelfth Day of August, 2003

JAMES E. ROGAN
*Director of the United States Patent and Trademark Office*